United States Patent
Schader et al.

(10) Patent No.: US 10,441,728 B2
(45) Date of Patent: Oct. 15, 2019

(54) NEEDLE SAFETY DEVICE AND DRUG DELIVERY DEVICE

(71) Applicant: Sanofi-Aventis Deutschland GmbH, Frankfurt am Main (DE)

(72) Inventors: Marc Schader, Frankfurt am Main (DE); Martin Vitt, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 529 days.

(21) Appl. No.: 15/037,919

(22) PCT Filed: Nov. 25, 2014

(86) PCT No.: PCT/EP2014/075557
§ 371 (c)(1),
(2) Date: Sep. 6, 2016

(87) PCT Pub. No.: WO2015/078868
PCT Pub. Date: Jun. 4, 2015

(65) Prior Publication Data
US 2016/0296713 A1    Oct. 13, 2016

(30) Foreign Application Priority Data
Nov. 28, 2013  (EP) .................................... 13194894

(51) Int. Cl.
*A61M 5/32* (2006.01)
(52) U.S. Cl.
CPC ........ *A61M 5/3245* (2013.01); *A61M 5/3204* (2013.01); *A61M 5/3243* (2013.01); *A61M 2005/3254* (2013.01)

(58) Field of Classification Search
CPC ........ A61M 2005/3254; A61M 5/3204; A61M 5/3243; A61M 5/3245
See application file for complete search history.

(56) References Cited

U.S. PATENT DOCUMENTS

2011/0023281 A1    2/2011  Schraga

FOREIGN PATENT DOCUMENTS

EP       2438939        4/2012
WO    WO2012/103140    8/2012
(Continued)

OTHER PUBLICATIONS

International Search Report and Written Opinion in International Application No. PCT/EP2014/075557, dated Feb. 27, 2015, 9 pages.

(Continued)

*Primary Examiner* — Brandy S Lee
(74) *Attorney, Agent, or Firm* — Fish & Richardson P.C.

(57) ABSTRACT

The invention refers to a needle safety device (1) comprising a needle cap (5) arranged to cover and protect a needle (4), a needle shield (6) relatively movable with respect to a drug delivery device (2) to cover and protect the needle (4) and a needle cap remover (7). The needle cap remover (7) has an outer part (8) adapted to be arranged to the needle shield (6) and an inner part (9) adapted to carry the needle cap (5), wherein the outer part (8) comprises a front end (10) having an opening (11) which at its edge exhibits a projection (12) directed inwards adapted to catch a front projection (13) of the inner part (9) and the inner part (9) comprises a back end (14) having a grip member (15) adapted to grip a back end (16) of the needle cap (5).

16 Claims, 6 Drawing Sheets

(56) References Cited

FOREIGN PATENT DOCUMENTS

| WO | WO2013/034984 | 3/2013 |
|----|---------------|--------|
| WO | WO2013/135566 | 9/2013 |

OTHER PUBLICATIONS

International Preliminary Report on Patentability in International Application No. PCT/EP2014/075557, dated May 31, 2016, 6 pages.
Rote Liste, "50. Hypophysen-, Hypothalamushormone, andere regulatorische Peptide u. ihre Hemmstoffe," Chapter 50, ed. 2008, 20 pages.

NEEDLE SAFETY DEVICE AND DRUG DELIVERY DEVICE

CROSS-REFERENCE TO RELATED APPLICATIONS

This application is a U.S. national stage application under 35 USC § 371 of International Application No. PCT/EP2014/075557, filed on Nov. 25, 2014, which claims priority to European Patent Application No. 13194894.5, filed on Nov. 28, 2013, the entire contents of which are incorporated herein by reference.

TECHNICAL FIELD

The invention relates to a needle safety device and a drug delivery device comprising such a needle safety device.

BACKGROUND OF THE INVENTION

Many drug delivery devices of the prior art, such as auto-injectors, syringes, have been developed for self-administration of the drug.

To protect the needle of the drug delivery device from damage or to protect people from needle-prick injuries before using of the device, the needle of the drug delivery device is covered by a protective needle cap or the so-called rigid needle shield (shortly named RNS).

In order to prepare the drug delivery device for delivering a dose the protective needle cap has to be removed from the needle. This may be done by gripping the protective needle cap and pulling it away from the needle. This will usually result in an exposed needle which is undesirable in terms of needle safety. In order to solve that problem the needle of the drug delivery device could be covered by a needle shield or shroud in a manner to hide the needle when the protective needle cap is removed.

SUMMARY OF THE INVENTION

Certain aspects of the invention relate to a needle safety device that reduces the risk of needle-prick injuries and needle damages before using the device and which may be easy to use and manufacture.

Preferred embodiments of the invention are given in the dependent claims.

According to the invention, a needle safety device for a drug delivery device comprises a needle cap arranged to cover and protect a needle of the drug delivery device and a needle cap remover having an outer part adapted to be arranged to the drug delivery device and an inner part adapted to carry the needle cap. The outer part comprises a front end having an opening which at its edge exhibits a projection directed inwards adapted to catch a front projection of the inner part so as to couple the outer part and the inner part. The inner part comprises a back end having a grip member adapted to grip a back end of the cap so as to couple the needle cap remover and the cap.

In the context of this specification, the term "back" or "proximal" end of a component or of a device refers to the end closest to the user's hand and the term "front" or "distal" end of a component or device refers to the end furthest from the user's hand.

The multi-part design of the needle cap remover comprising the inner and the outer part which are coupled to each other by corresponding projections allows a limited setting range of the needle cap remover. In a possible embodiment, the outer part of the needle cap remover is designed as an outer cap which covers and protects the inner needle shield and thus prevents an early movement of the needle shield.

In an exemplary embodiment, the projection of the outer part is formed as at least two opposite arms which ends are angled. In particular, the ends of the opposite arms could be angled away from each other or otherwise to engage the corresponding front projection of the inner part. Depending on the material of the inner and outer part of the needle cap remover, at least one of the parts, in particular the opposite arms or the front projection are flexible, e.g. are made of a flexible material or soft plastic. Due to a flexible design of the angled ends, the flexible arms of the outer part could be linked to the inner part in such a manner that they are pivoted or swiveled to approach each other so that they are carried over the rigid front projection of the inner part when the outer part is assembled onto or into the inner part. Otherwise, the flexible front projection may be pivoted or swiveled away from each other by the rigid arms of the outer part when the outer part is assembled to the inner part, e.g. onto or into the inner part. After assembling of the outer and inner parts, the front projection of the inner part and the projection of the outer part are correspondingly inclined to each other in such a manner that they are coupled to each other to allow a common axial movement after assembling.

In a possible embodiment, the front projection of the inner part is correspondingly formed to the projection of the outer part. In particular the front projection of the inner part is formed as at least two protruding tabs. The protruding tabs are protruded from the inner surface of the inner part and are directed inwards in an angle to be gripped by the also angled ends of the arms of the outer part. During assembling of the outer part onto or into the inner part, the angled ends of the arms and the angled protruding tabs of the front projection are coupled and engaged by a positive-locking connection and/or form-fitting connection, e.g. snap-fit-connection or latching connection.

According to a further embodiment, the front projection of the inner part is formed as a dome. The dome may be circumferentially formed on the inner surface of the inner part. Alternatively, multiple domes, e.g. multiple opposite curvatures, may be formed on the inner surface of the inner part. In other words, the dome is protruded from the inner surface of the inner part and directed inwards and is formed e.g. as an encircling edge with a rounded underside for guiding the projection of the outer part during assembling of the needle safety device.

In yet a further embodiment, the front projection of the inner part is formed as flexible legs or a stem with flexible legs which protrude from the front of the inner part and directed inwards through the opening of the outer part.

According to another embodiment of the invention, the grip member of the inner part is formed as a back projection of the inner part. The back projection bents into the inner part to engage the back end of the needle cap by a positive-locking connection and/or form-fitting connection. In particular, the back projection is formed as at least two legs directed inwards to engage the back end of the needle cap.

According to an alternative embodiment, the grip member of the inner part of the needle cap remover is formed with a profiled surface adapted to grip lateral surfaces of the cap e.g. by friction connection and/or positive-locking connection and/or form-fitting connection. In particular, the inner surface of the inner part is roughened or lightly ribbed or grooved or coated by a soft coating material.

Alternatively or additionally, the needle cap has an outer surface comprising grip elements adapted to be gripped by the grip member of the inner part of the needle cap remover e.g. by positive-locking connection and/or form-fitting connection and/or friction connection. In particular, the grip elements of the needle cap may be formed as a profiled outer surface, e.g. as ribs, hooks, domes, grooves and/or protruding pegs, arms, borders or ledges. The coupling between the inner part of the needle cap remover and the needle cap is designed in such a manner that after assembling during an axial movement of the needle cap remover the needle cap is removed from the needle together with the needle cap remover.

According to another embodiment of the invention, the needle cap and the needle cap remover are made from plastic materials with the same or different strengths. In particular, the needle cap is made of a rigid plastic material to protect the needle against damages. The needle cap is also called protective needle shield or rigid needle shield (shortly named RNS). The needle cap remover is preferably made of a rigid plastic material, e.g. polypropylene. Alternatively, the needle cap may be made from a soft elastomer, for example rubber or a thermoplastic elastomer (TPE), for a tight grip and a good seal between the needle cap and the drug delivery. The needle cap remover is rigid and is made from polypropylene for a good protection against needle damages before use and to keep the needle sterile.

According to the invention, a drug delivery device comprising a needle safety device described above allows an easy assembling of the needle cap remover during manufacturing and a safe removing of the needle cap before use without earlier movement of the needle shield and with a given setting range for the needle cap remover.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limitive of the present invention, and wherein.

Corresponding parts are marked with the same reference symbols in all figures.

DETAILED DESCRIPTION OF PREFERRED EMBODIMENTS

Figure 1:
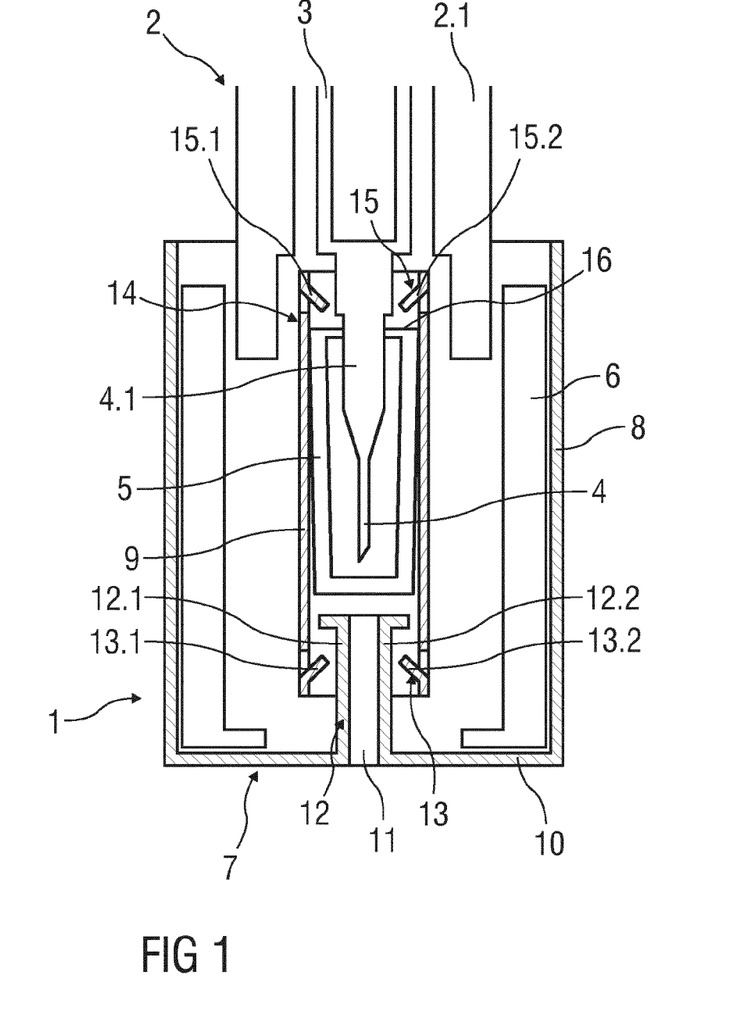
FIG. 1 shows a longitudinal section of an exemplary embodiment of a needle safety device for a drug delivery device.

FIG. 1 shows one embodiment of the present invention in a longitudinal section of a needle safety device 1 for a drug delivery device 2.

The drug delivery device 2 is a pre-filled syringe 3 having a needle 4. The needle 4 may be fixed to the distal end of the syringe 3 or removable therefrom, as a matter of design choice. The syringe 3 is hold in a housing 2.1 of the drug delivery device 2. Alternatively, the drug delivery device could be an auto-injector or a syringe to be filled.

The needle safety device 1 comprises a needle cap 5, a needle shield 6 and a needle cap remover 7 which are adapted to be connected to each other by friction connection and/or positive locking connection and/or form-fitting connection. As it can be seen, the needle shield 6 is being mounted on the housing 2.1 of the drug delivery device 2 in a movable manner and the needle cap 5 is being mounted on the needle 4 in a separable manner. The needle cap remover 7 is being mounted on the needle cap 5 in a secured manner and on the drug delivery device 2, in particular on the needle shield 6 in a separable manner.

As not shown in the longitudinal sections of the needle safety device 1, the components, in particular the needle cap remover 7 with the inner part 8 and the outer part 9 as well as the needle cap 5, have tubular or cylindrical shapes. They may be having different shapes and may have oval or polygonal shapes in cross section.

In detail, the needle cap 5 is arranged to a needle hub 4.1 to cover and protect the needle 4. The needle cap 5 may be connected to a needle hub 4.1 of the needle 4 by means of a friction connection and/or positive locking connection. The needle cap 5 is preferably of a rigid material and is also called as a protective needle shield or rigid needle shield (shortly named RNS). Alternatively, the needle cap is made of a resilient material, especially of a soft elastomer, for example rubber or a thermoplastic elastomer (TPE).

The needle shield 6 covers and protects the needle 4 before, during and after use. The needle shield 6 is movably arranged with respect to the housing 2.1 of the drug delivery device 2. In the shown embodiment, the needle shield 6 is provided at the distal or front end of the housing 2.1. In particular, the needle shield 6 is arranged onto the housing 2.1. Alternatively, the needle shield 6 could be arranged into the housing 2.1.

As shown in FIG. 1, the needle shield 6 is in the advanced position in which the needle 4 is covered. In this advanced position before use, the needle shield 6 is hold by a positive connection and/or a friction connection and/or a form-fitting connection, e.g. a snap-fit connection. During use, the needle shield 6 is movable from the advanced position to a retracted position (not shown). After use, the needle shield 6 is movable back to the advanced position in which the needle shield 6 is secured with respect to the housing 2.1.

The needle cap remover 7 comprises at least an outer part 8 and an inner part 9 which are non-releasably coupled to each other after assembling. The outer part 8 is adapted to be arranged at the needle shield 6 and is formed as a gripping cap. Preferably, the outer part 8 is releasably coupled to the needle shield 6 by a friction connection and/or a form-fitting connection.

The inner part 9 is adapted to carry the needle cap 5 by a friction connection and/or a positive locking connection and forms a so-called RNS remover of the needle safety device 1 because the inner part 9 is coupled to the needle cap 5 in such a secured manner that if the inner part 9 is axially moved away from the drug delivery device 2 it takes the needle cap 5 with.

Due to the coupling of the outer part 8 with the inner part 9 and the inner part 9 with the needle cap 5, the needle cap 5 is removed from the needle 4 when the outer part 8 is removed from the drug delivery device 1.

The outer part 8 comprises a front end 10 having an opening 11 which at its edge exhibits a projection 12 directed inwards.

The inwardly directed projection 12 is adapted to catch a front projection 13 of the inner part 9 so as to couple the outer part 8 to the inner part 9. The inner part 9 which forms the rigid needle shield comprises a back end 14. The back end 14 has a grip member 15 adapted to grip a back end 16 of the needle cap 5 so as to couple the needle cap remover 2 to the needle cap 5.

The grip member 15 is designed as a back projection directed inwards into the inner part 9. The back projection bents into the inner part in such a manner that the end of the back projection engages the back end 16 of the needle cap 5 by a positive-locking connection and/or form-fitting connection. In particular, the back projection is formed as at least two legs 15.1, 15.2 directed inwards to engage the back end 16 of the needle cap 5.

The multi-part design of the needle cap remover 2 with the inner and outer parts 8 and 9 which are coupled to each other by corresponding projections 12, 13 allows a limited setting range of the needle cap remover 7. In a possible embodiment the outer part 8 of the needle cap remover 7 is designed as an outer cap which covers and protects the inner needle shield 6 and thus prevents an early movement of the needle shield 6.

In an exemplary embodiment, the projection 12 of the outer part 8 is designed as at least two opposite arms 12.1, 12.2 which free ends are angled. In particular, the ends of the opposite arms 12.1, 12.2 are angled away from each other to engage the corresponding front projection 13 of the inner part 9. Depending on the material of the inner and outer part 8, 9 of the needle cap remover 7, at least one of the parts, in particular the opposite arms 12.1, 12.2 of the outer part are flexible, e.g. are made of a flexible or soft plastic material. Alternatively, the opposite arms 12.1, 12.2 are rigid and the front projection 13 is made of a flexible material.

Due to the flexible design of the arms 12.1, 12.2 with the angled ends, the flexible arms 12.1, 12.2 could be pivoted or swiveled to approach each other and thus come closer on to another so that they are carried over the rigid front projection 13 of the inner part 9 when the outer part 8 is assembled to the inner part 9.

Otherwise, the flexible front projection 13 may be pivoted or swiveled away from each other by the rigid arms 12.1, 12.2 of the rigid outer part 8 when the outer part 8 is assembled to the inner part 9. After assembling of the outer and inner part 8, 9 the front projection 13 of the inner part 9 and the projection 12 of the outer part 8 are correspondingly inclined to each other in such a manner that they are coupled to each other to allow a common axial movement.

As it is shown in FIG. 1, the front projection 13 of the inner part 9 is correspondingly formed to the projection 12 of the outer part 8. In particular the front projection 13 is formed as at least two protruding tabs 13.1, 13.2. The protruding tabs 13.1, 13.2 are protruded from the inner surface of the inner part 9 and are directed inwards in an angle to be gripped by the also angled ends of the arms 12.1, 12.2 of the outer part 8.

After assembling of needle cap remover 7, the angled ends of the arms 12.1, 12.2 and the angled protruding tabs 13.1, 13.2 are coupled and securely engaged, wherein the tabs 13.1, 13.2 define a stop on which the arms 12.1, 12.2 come in abutment in such a manner that when the outer part 8 is griped and removed from the needle shield 6 the inner part 9 moves too to remove the needle cap 5 from the needle 4. In particular, the arms 12.1, 12.2 and the protruding tabs 13.1, 13.2 are securely engaged by a positive-locking connection and/or form-fitting connection, e.g. snap-fit-connection or latching connection.

The protruding tabs 13.1, 13.2 as well as the grip member 15 of the inner part 9 are disposed in openings of the inner part 9 enabling at least the tabs 13.1, 13.2 to be slightly pivoted or swiveled with regard to the inner part 9 as well as the outer part 8 or needle cap 5 during assembling or removing.

Figure 2:
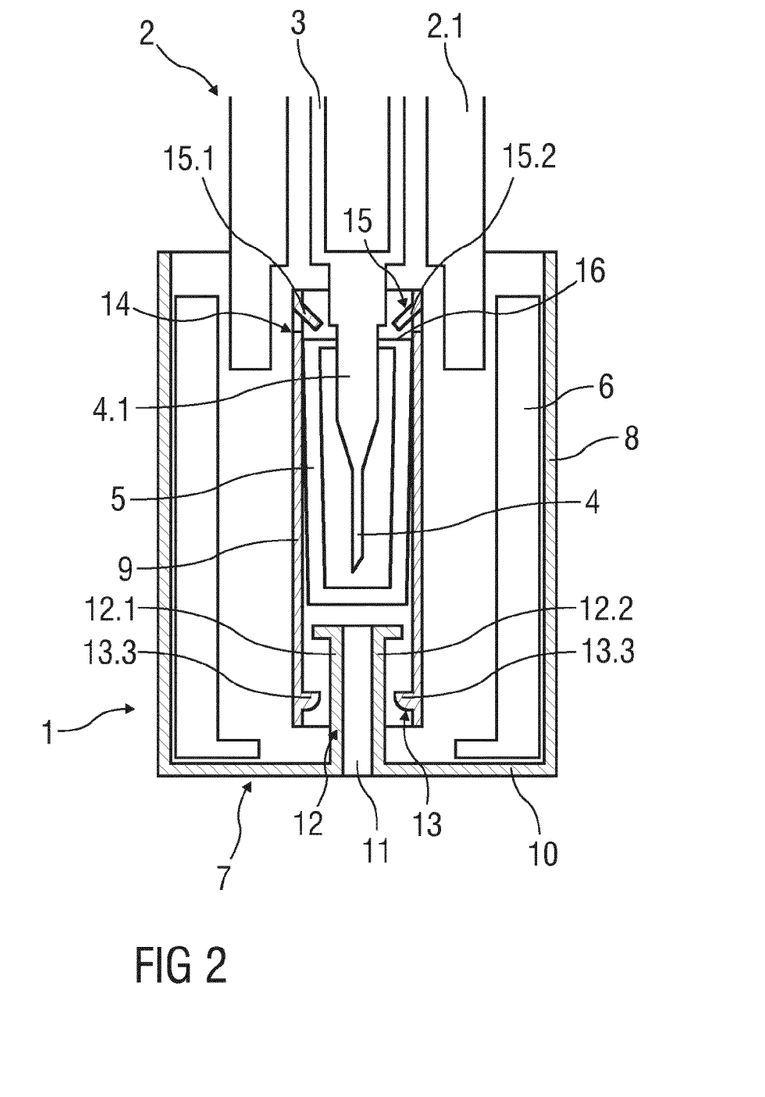
FIGS. 2 to 6 show longitudinal sections of different embodiments of a needle safety device for a drug delivery device.

FIG. 2 shows a further embodiment of the invention. The invention differs in the kind of the front projection 13 of the inner part 9. The front projection 13 is designed as a dome 13.3. The dome 13.3 may be formed as circumferential edge on the inner surface of the inner part 9.

Alternatively, multiple domes, e.g. multiple opposite curvatures, may be formed on the inner surface of the inner part (not shown). In other words, the dome 13.3 is protruded from the inner surface of the inner part 9 and directed to the inside of the tubular inner part 9 towards the angled ends of the arms 12.1, 12.2.

The underside of the dome 13.3 is rounded to support the guiding of the projection 12 of the outer part 8 during assembling. The topside of the dome 13.3 is planar to provide a stop surface for the angled ends of the arms 12.1, 12.2.

Figure 3:
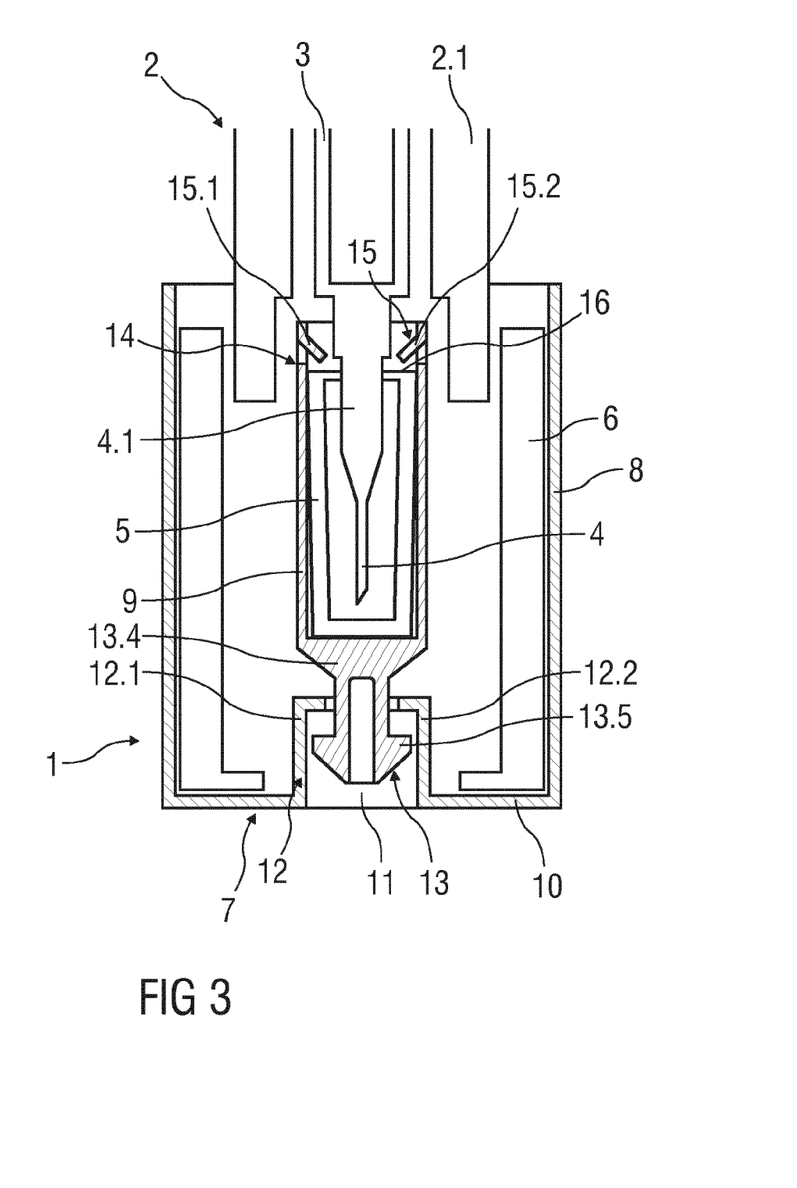

FIG. 3 shows yet a further embodiment. The invention according to this embodiment also differs in the kind of the front projection 13 of the inner part 9. The front projection 13 of the inner part 9 is formed as a stem 13.4 with flexible legs 13.5. The flexible legs 13.5 protrude from the front or distal end of the inner part 9 into the distal direction and direct inwards through the opening 11 of the outer part 8.

The free ends of the flexible legs 13.5 comprise hooks 13.5.1 which cooperate with complementary angled ends of the arms 12.1, 12.2 of the outer part 8. When the outer part 8 is griped and removed from the needle shield 6 to remove the needle cap 5 from the needle 4, the hooks 13.5.1 are engaged with the angled ends of the arms 12.1, 12.2 and the inner part 9 as well as the needle cap 5 are removed too from the drug delivery device 2.

Figure 4:
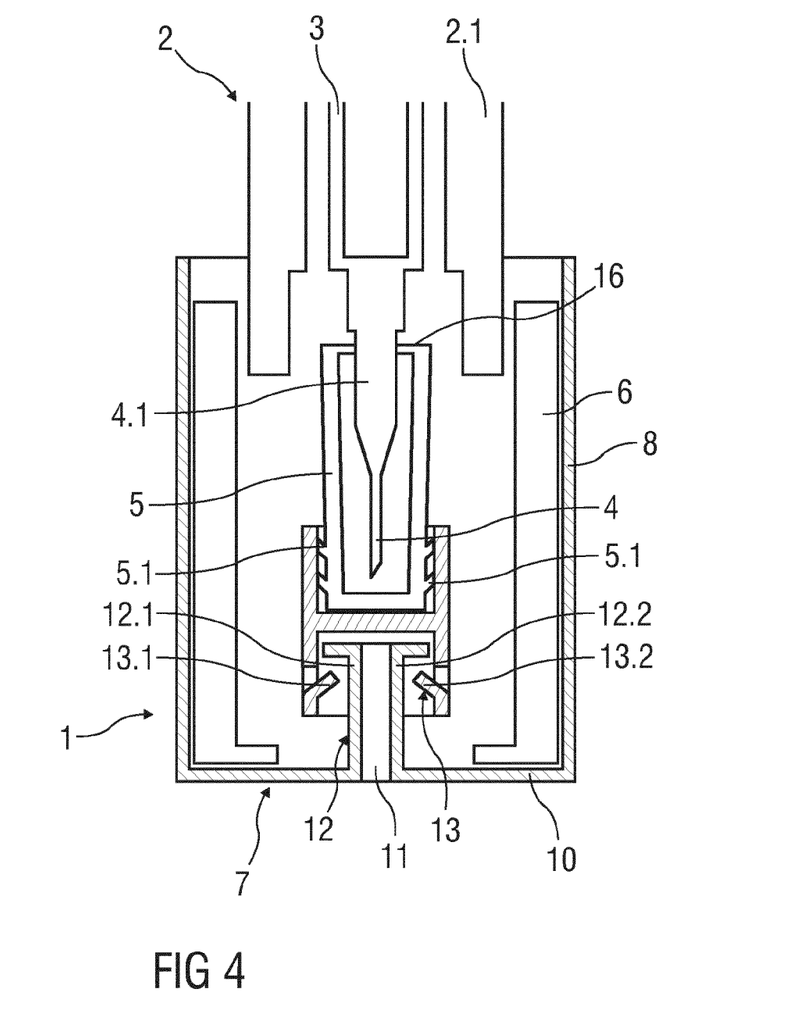

FIG. 4 shows another embodiment of the invention. The invention according to this embodiment differs in the kind of the grip member 15 of the inner part 9.

The grip member 15 of the inner part 9 is formed with a profiled surface adapted to grip lateral surfaces of the needle cap 5 e.g. by friction connection and/or positive-locking connection and/or form-fitting connection. In particular, the inner surface of the inner part 9 may be roughened or lightly ribbed or grooved or coated with a coating material so that the inner surface is softened.

Additionally, the needle cap 5 has grip elements 5.1 on the outer surface. The grip elements 5.1 are adapted to be gripped by the grip member 15 of the inner part 9 e.g. by positive-locking connection and/or form-fitting connection and/or friction connection. As shown in FIG. 4, the grip elements 5.1 are formed as hooks.

Alternatively, the grip elements 5.1 may be formed as a profiled outer surface, e.g. as ribs, domes, grooves and/or protruding pegs, arms. The coupling between the inner part 9 and the needle cap 5 is designed in such a manner that after assembling during an axial movement of the needle cap remover 7 the needle cap 5 is removed from the needle 4 together with the needle cap remover 7 and thus with the inner and outer parts 9, 8.

Figure 5:
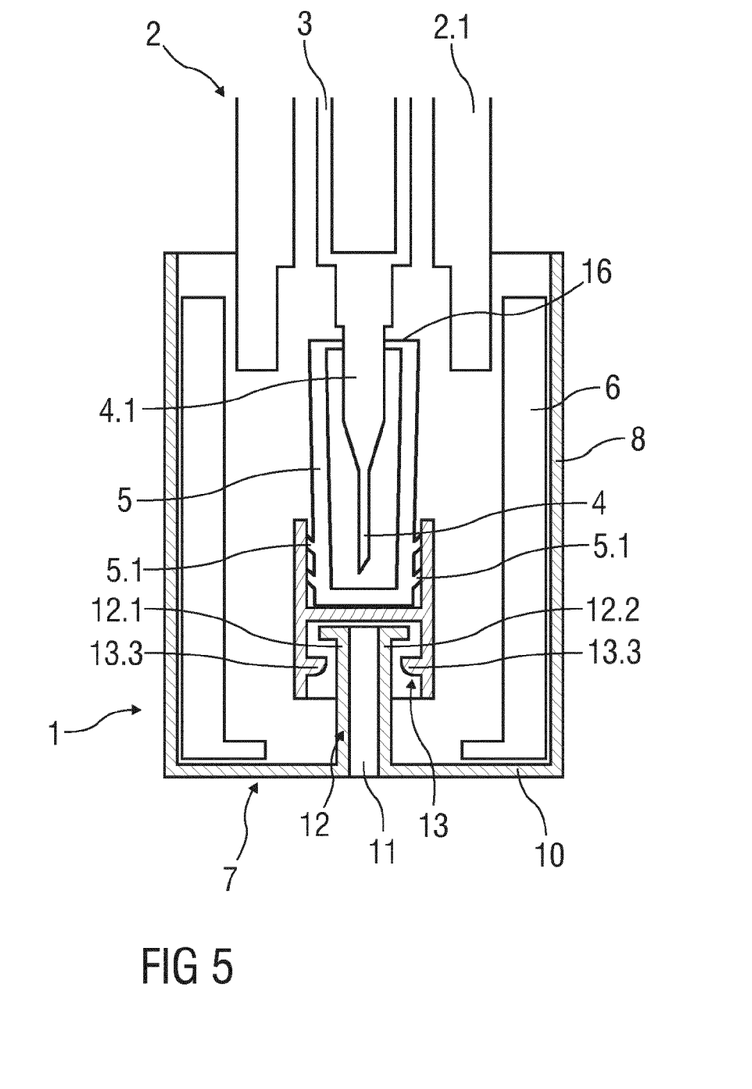
Figure 6:
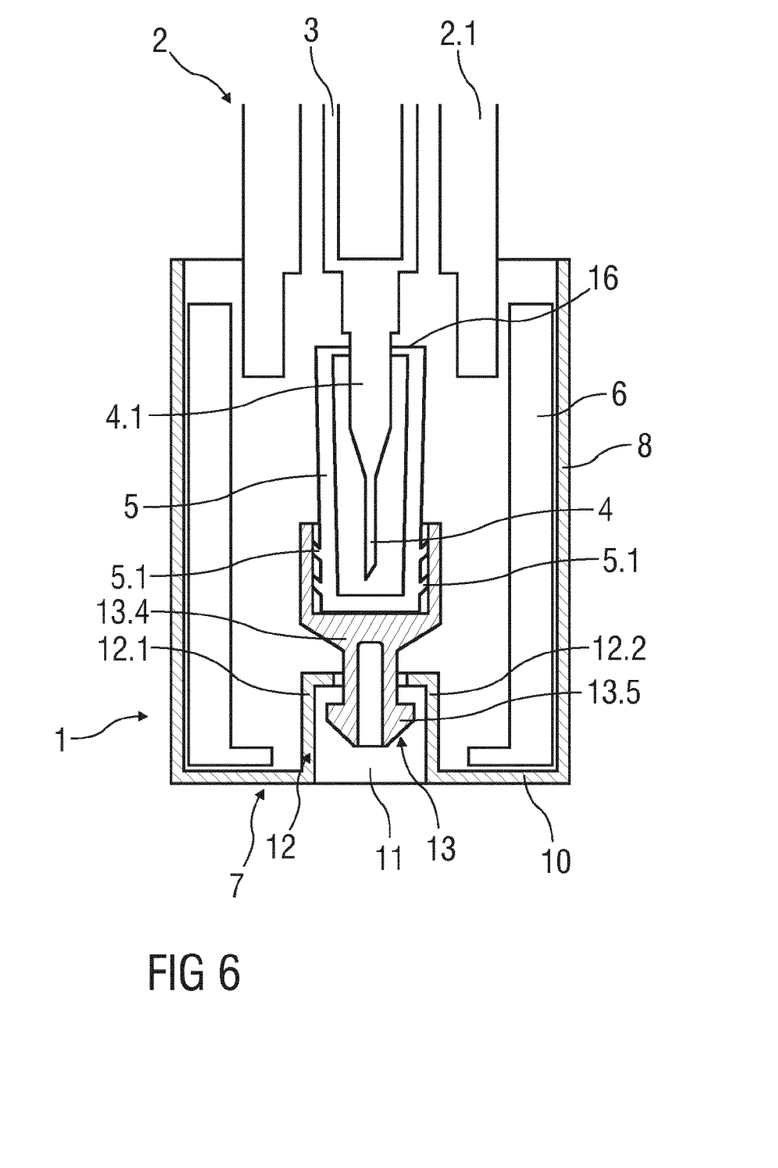

FIGS. 5 and 6 show further embodiments with possible combinations of different couplings of the inner part 9 and the outer part 8 as well as the different couplings of the inner part 9 and the needle cap 5.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the abovementioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Gl u-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36[Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-Nh2,
des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(02)25, Asp28] Exendin-4(S1-39)-(Lys)6-NH2, H-Asn-(Glu)5-des Pro36, Pro37, Pro38 [Met(O)14, Trp (02)25, Asp28] Exendin-4(1-39)-(Lys)-6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kD) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES

1 Needle safety device
2 Drug delivery device
3 Syringe
4 Needle
4.1 Needle hub
5 Needle cap
5.1 Grip elements 6 Needle shield
7 Needle cap remover
8 Outer part
9 Inner part
10 Front end
11 Opening
12 Projection of the outer part
12.1, 12.2 Arms
13 Front projection of the inner part
13.1, 13.2 Protruding tabs
13.3 Dome
13.4 Stem
13.5 Legs
13.5.1 Hooks
14 Back end of the inner part
15 Grip member of the inner part
15.1, 15.2 Legs
16 Back end of the needle cap

The invention claimed is:

1. A needle safety device for a drug delivery device comprising:
a needle cap arranged to cover and protect a needle of the drug delivery device;
a needle cap remover having:
an outer part adapted to be secured to the drug delivery device; and
an inner part adapted to carry the needle cap;
wherein the outer part comprises a front end having an opening which at an edge of the opening exhibits a projection directed inwards adapted to catch a front projection of the inner part; and
the inner part comprises a back end having a grip member adapted to grip a back end of the needle cap, wherein the projection of the outer part is formed as at least two opposite arms having angled ends.

2. The needle safety device according to claim 1, wherein the front projection of the inner part is formed as at least two protruding tabs corresponding to the projection of the outer part.

3. The needle safety device according to claim 1, wherein the front projection of the inner part is formed as a dome corresponding to the projection of the outer part.

4. The needle safety device according to claim 1, wherein the front projection of the inner part is formed as legs corresponding to the projection of the outer part.

5. The needle safety device according to claim 1, wherein the grip member of the inner part is formed as a back projection of the inner part.

6. The needle safety device according to claim 1, wherein the grip member of the inner part is formed as a profiled surface adapted to grip lateral surfaces of the needle cap by friction.

7. The needle safety device according to claim 1, wherein the needle cap has an outer surface comprising grip elements adapted to be gripped by the grip member of the inner part of the needle cap remover.

8. The needle safety device according to claim 7, wherein the grip elements are formed as a profiled outer surface of the needle cap and/or protruding pegs.

9. The needle safety device according to claim 1, wherein the needle cap and the needle cap remover are made from plastic materials with different strengths.

10. The needle safety device according to claim 9, wherein the needle cap is made from a soft elastomer.

11. The needle safety device according to claim 9, wherein the needle cap remover is rigid and is made from polypropylene.

12. The needle safety device of claim 1, wherein: i) the at least two opposite arms are flexible, ii) the front projection is flexible, or iii) the at least two opposite arms and the front projection are flexible.

13. A drug delivery device comprising:
a housing
a needle; and
a needle safety device comprising:
needle cap arranged to cover and protect the needle;
a needle cap remover having:
an outer part adapted to be secured to the housing of the drug delivery device, and
an inner part adapted to carry the needle cap,
wherein the outer part comprises a front end having an opening which at an edge of the opening exhibits a projection directed inwards adapted to catch a front projection of the inner part, and
the inner part comprises a back end having a grip member adapted to grip a back end of the needle cap, wherein the projection of the outer part is formed as at least two opposite arms having angled ends.

14. The drug delivery device of claim 13, further comprising a cartridge containing a pharmaceutically active compound.

15. A method of removing a needle cap from a needle of a drug delivery device, the method comprising:
gripping an outer surface of a needle cap remover of the drug delivery device; the needle cap remover having an outer part and an inner part, wherein the outer part comprises a front end having an opening which at an edge of the opening exhibits a projection directed inwards adapted to catch a tab of the inner part, wherein the inner part comprises a back end having a grip member adapted to grip a back end of the needle cap, wherein the projection of the outer part is formed as at least two opposite arms having angled ends; and
pulling the needle cap remover distally from the drug delivery device such that the projection of the outer part of the needle cap remover contacts tabs of the inner part of the needle cap remover and pulls the inner part distally, the grip member of the inner part contacting the needle cap and pulling the needle cap distally with the inner part.

16. The drug delivery device of claim 13, wherein: i) the at least two opposite arms are flexible, ii) the front projection is flexible, or iii) the at least two opposite arms and the front projection are flexible.

* * * * *